United States Patent
Yu

(10) Patent No.: US 10,443,093 B2
(45) Date of Patent: *Oct. 15, 2019

(54) FLUOROUS OLIGONUCLEOTIDE MICROARRAY

(71) Applicant: MS² ARRAY LLC, Pittsburgh, PA (US)

(72) Inventor: Marvin Yu, Pittsburgh, PA (US)

(73) Assignee: MS2 ARRAY LLC, Pittsburgh, PA (US)

(*) Notice: Subject to any disclaimer, the term of this patent is extended or adjusted under 35 U.S.C. 154(b) by 53 days.

This patent is subject to a terminal disclaimer.

(21) Appl. No.: 15/360,066

(22) Filed: Nov. 23, 2016

(65) Prior Publication Data

US 2017/0073743 A1 Mar. 16, 2017

Related U.S. Application Data

(63) Continuation-in-part of application No. 14/394,435, filed on Oct. 14, 2014, now Pat. No. 9,977,019.

(60) Provisional application No. 62/259,177, filed on Nov. 24, 2015.

(51) Int. Cl.
| | |
|---|---|
| *G01N 33/543* | (2006.01) |
| *G01N 33/58* | (2006.01) |
| *C12Q 1/6837* | (2018.01) |
| *B01J 19/00* | (2006.01) |
| *C40B 50/18* | (2006.01) |

(52) U.S. Cl.
CPC ........ *C12Q 1/6837* (2013.01); *B01J 19/0046* (2013.01); *B01J 2219/0063* (2013.01); *B01J 2219/00454* (2013.01); *B01J 2219/00596* (2013.01); *B01J 2219/00608* (2013.01); *B01J 2219/00626* (2013.01); *B01J 2219/00632* (2013.01); *B01J 2219/00659* (2013.01); *B01J 2219/00722* (2013.01); *C40B 50/18* (2013.01)

(58) Field of Classification Search
None
See application file for complete search history.

(56) References Cited

U.S. PATENT DOCUMENTS

| | | | |
|---|---|---|---|
| 4,885,250 | A | 12/1989 | Eveleigh et al. |
| 4,954,444 | A | 9/1990 | Eveleigh et al. |
| 5,525,264 | A | 6/1996 | Cronin et al. |
| 5,777,121 | A | 7/1998 | Curran et al. |
| 5,859,247 | A | 1/1999 | Curran et al. |
| 6,156,896 | A | 12/2000 | Curran et al. |
| 6,673,539 | B1 | 1/2004 | Wipf et al. |
| 2001/0031469 | A1 | 10/2001 | Volinia |
| 2009/0149343 | A1 | 6/2009 | Nightingale |
| 2010/0016171 | A1 | 1/2010 | Wong et al. |
| 2010/0159604 | A1 | 6/2010 | Pohl et al. |
| 2013/0115430 | A1 | 5/2013 | Ober et al. |

FOREIGN PATENT DOCUMENTS

| | | |
|---|---|---|
| WO | WO 2002083933 A2 | 10/2002 |
| WO | WO 2004035744 A2 | 4/2004 |
| WO | WO 2006009494 A1 | 1/2006 |
| WO | WO 2011109368 A2 | 9/2011 |

OTHER PUBLICATIONS

Nucleoside From Wikipedia, the free encyclopedia; pp. 1-2 downloaded on Jul. 24, 2018.*
Beller et al Noncovalent Attachment of Nucleotides by FluorousFluorous Interactions: Application to a Simple Purification Principle for Synthetic DNA Fragments Helvetica Chimica Acta ± vol. 88 (2005) pp. 171-179.*
Fluorous Technologies Fluorous Immobilization for Microarray Formation pp. 1-2, downloaded on Jan. 4, 2017.
Ko et al., Fluorous-Based Carbohydrate Microarrays J. Am. Chem. Soc. 2005, 127, 13162-13163.
Electrical resistivity and conductivity from Wikipedia, the free encyclopedia pp. 1-19; downloaded on Jan. 4, 2017.
Zhong et al., Solid-Phase Synthesis of Arginine-Containing Peptides by Guanidine Attachment to a Sulfonyl LinkerJ. Org. Chem. 1997, 62, 9326-9330.
Fluorous Microarrays (Fluorous Technologies, Inc.) downloaded on Jan. 4, 2017 pp. 1-2.
Fluorous Microarrays (Fluorous Technologies, Inc.) downloaded on Aug. 23, 2016.
Baker et al., Journal of Environmental Management 92 (2011) 2781-2785.

(Continued)

*Primary Examiner* — Maria G Leavitt
(74) *Attorney, Agent, or Firm* — Frost Brown Todd LLC

(57) ABSTRACT

A fluorous-modified composition, a fluorous nucleoside, nucleotide, or oligonucleotide microarray, a compositional detection process, a process of forming a fluorous nucleoside, nucleotide, or oligonucleotide microarray, and fluorous nucleoside, nucleotide, or oligonucleotide microarray processes are disclosed. The fluorous-modified composition includes a linker, a nucleoside, nucleotide, or oligonucleotide connected to the linker, and a fluorous domain connected to the linker. The fluorous-modified composition includes at least one terminal perfluoroalkyl group in the fluorous domain, a solid-phase attachment group connected to the linker, or a combination thereof. The compositional detection process includes using the fluorous microarray for compositional detection. The processes of forming a fluorous microarray include transfer blotting the fluorous-modified composition to form a fluorous microarray and the spotting of reaction mixtures containing a fluorous-modified nucleoside, nucleotide, or oligonucleotide. The fluorous microarray includes a fluorous-modified conductive surface and fluorous nucleoside, nucleotide, or oligonucleotides positioned on the fluorous-modified surface. The fluorous microarray process includes using information corresponding to a compositional detection process.

5 Claims, 9 Drawing Sheets

(56) References Cited

OTHER PUBLICATIONS

Wang et al., Surface Modification of Poly(dimethylsiloxane) with a Perfluorinated Alkoxysilane for Selectivity toward Fluorous Tagged Peptides Langmuir 2008, 24, 1080-1086.
E.P. Go, "Selective Metabolite and Peptide Capture/Mass Detection using Fluorous Affinity Tags", Journal of Proteome Research, 2007, 6, pp. 1492-1499, copyright 2007 American Chemical Society, published on Web Mar. 8, 2007.
P.N. Blit, et al., "Surface Immobilization of Elastin-like Polypeptides using Fluorinated Surface Modifying Additives", Journal of Biomedical Materials Research, Part A, vol. 96A, No. 4, Mar. 15, 2011, pp. 648-662.
C.C. Larsen et al., "The effect of RGD fluorosurfactant polymer modification of ePTFE on endothelial cell adhesion, growth and function", Biomaterials, vol. 27, No. 28, Oct. 1, 2006, pp. 4846-4855, Elsevier Science Publishers BV., Barking, GB.
D. Wang, "Surface Modification and Characterization of Poly(dimethylsiloxane) with a Perfluorinated Alkoxysilane for Selectivity Towards Fluorous Tagged Peptides", Queens's University—Thesis Master of Science, May 1, 2008, retrieved from the Internet: URL:http://qspace.library.queensu.ca/bitstream/1974/1205/1/Wang_Dan_200805_MSc.pdf, pp. 32, 33, 43, 67 and 80, figures 3.13-3.16.
A. Nordstrom et al., "Surfactant-enhanced desorption/ionization on silicon mass spectrometry, Analytical Chemistry", vol. 78, No. 1, Jan. 1, 2006, pp. 272-278, American Chemical Society.
G. Macbeath, "Printing Proteins as Microarrays for High-Throughput Function Determination", Science Magazine, Sep. 8, 2000, vol. 289, pp. 1760-1762.
P. Voigt, "Histone Tails: Ideal Motifs for Probing Epigenetics through Chemical Biology Approaches", ChemBioChem 2011, vol. 12, pp. 236-252, copyright 2011 Wiley-VCH Verlag GmbH & Co. KGaA, Weinheim.
S. Chang, "Glycan Array on Aluminum Oxide-Coated Glass Slides through Phosphonate Chemistry", Journal of American Chemical Society, 2010, vol. 132, pp. 13371-13380, copyright 2010 American Chemical Society.
Z.A. Gurard-Levin, "Combining Mass Spectrometry and Peptide Arrays to Profile the Specificities of Histone Deacetylases", ChemBioChem 2009, vol. 10, pp. 2159-2161, copyright 2009 Wiley-VCH Verlag GmbH & Co. KGaA, Weinheim.
B.Y.M. Collet, "Fluorous-based peptide microarrays for protease screening", Journal of Fluorine Chemistry, 2009, copyright 2009 Elsevier B.V.
A.J. Vegas, "Fluorous-Based Small-Molecule Microarrays for the Discovery of Histone Deacetylase Inhibitors", Angew. Chem. Int. Ed. 2007, vol. 46, pp. 1-6, copyright 2007 Wiley-VCH Verlag GmbH & Co. KGaA, Weinheim.
J. Kim, "Tudor, MBT and chromo domains gauge the degree of lysine methylation", EMBO reports vol. 7, No. 4, 2006, pp. 397-403, copyright 2006 European Molecular Biology Organization.
S. Himpel, "Specificity Determinants of Substrate Recognition by the Protein Kinase DYRK1A", The Journal of Biological Chemistry, vol. 275, No. 4, Issue of Jan. 28, pp. 2431-2438, 2000, copyright 2000 by the American Society for Biochemistry and Molecular Biology, Inc.
X. Espanel, "Mapping of Synergistic Components of Weakly Interacting Protein-Protein Motifs Using Arrays of Paired Peptides", The Journal of Biological Chemistry, vol. 278, No. 17, Issue of Apr. 25, pp. 15162-15167, 2003, copyright 2003 by the American Society for Biochemistry and Molecular Biology, Inc.
S.E. Hutchinson, "Enabling Lead Discovery for Histone Lysine Demethylases by High-Throughput Rapid Fire Mass Spectrometry", Journal of Biomolecular Screening, published online Aug. 21, 2011 Sage Publications, pp. 1-9.

T.R. Northen, "A Nanostructure-Initiator Mass Spectrometry-Based Enzyme Activity Assay", PNAS, Mar. 11, 2008, vol. 105, No. 10, pp. 3678-3683, www.pnas.org/cgi/doi/10.1073/pnas.0712332105.
K. Ko, "Fluorous-Based Carbohydrate Microarrays", J. Am. Chem. Soc. 2005, vol. 127, pp. 13162-13163, 2005 American Chemical Society.
S.S. Oliver, Dynamic Interplay between Histone H3 Modifications and Protein Interpreters: Emerging Evidence for a Histone Language-, ChemBioChem 2011, vol. 12, pp. 299-307, copyright 2011 Wiley-VCH Verlag GmbH & Co. KGaA, Weinheim.
M. Kacevska, "Perspectives on Epigenetics and its Relevance to Adverse Drug Reactions, Clinical Pharmacology & Therapeutics", vol. 89, No. 6, Jun. 2011, pp. 902-907, advance online publication Apr. 20, 2011, Nature Publishing Group, www.nature.com/cpt.
A. Petronis, "Epigenetics as a Unifying Principle in the Aetiology of Complex Traits and Diseases", Nature, vol. 465, Jun. 10, 2010, pp. 721-727, 2010 Macmillan Publishers Limited.
J Comley, "Epigenetics, an Emerging Target Class for Drug Screening", Drug Discovery World, Spring 2011, pp. 40-55.
A.J. Flavell, "A Microarray-based High Throughput Molecular Marker Genotyping Method: The Tagged Microarray Marker (TAM) Approach", Nucleic Acids Research, 2003, vol. 31, No. 19, pp. 1-8, Oxford University Press 2003, downloaded from http://nar.oxfordjournals.org/ at University of Pittsburgh on Apr. 3, 2012.
Y. Ito, "Solid-phase Oligosaccharide Synthesis and Related Technologies", Chemical Biology 1998, 2:701-708, http://biomednet.com/elecref/13675931002000701, Current Biology Ltd, ISSN 1367-5931.
B. B. Haab, "Methods and Applications of Antibody Microarrays in Cancer Research", Proteomics 2003, 3, 2116-2122, 2003 Wiley-VCH Verlag GmbH & Co. KGaA, Weinheim.
J.S. Shumaker-Parry, "Microspotting Streptavidin and Double-Stranded DNA Arrays on Gold for High-Throughput Studies of Protein—DNA Interactions by Surface Plasmon Resonance Microscopy", Analytical Chemistry, vol. 76, No. 4, Feb. 15, 2004, pp. 918-929, 2004 American Chemical Society, Published on Web Jan. 9, 2004.
S.M. Brittain, "Enrichment and Analysis of Peptide Subsets using Fluorous Affinity Tags and Mass Spectrometry", Nature Biotechnology, Advance Online Publication, pp. 1-6, Published online Mar. 13, 2005, 2005 Nature Publishing Group, http://www.nature.com/naturebiotechnology.
C. Beller, "Noncovalent Attachment of Nucleotides by Fluorous—Fluorous Interactions: Application to a Simple Purification Principle for Synthetic DNA Fragments", Helvetica Chimica Acta, vol. 88 (2005), pp. 171-179, 2005 Verlag Helvetica Chimica Acta AG, Zurich.
P. C. de Visser, "A Novel, Base-Labile Fluorous Amine Protecting Group: Synthesis and Use as a Tag in the Purification of Synthetic Peptides", Tetrahedron Letters 44 (2003) pp. 9013-9016, 2003 Elsevier Ltd.
Z. A. Gurard-Levin, "The Activity of HDAC8 Depends on Local and Distal Sequences of its Peptide Substrates", Biochemistry 2008, 47, 6242-6250, 2008 American Chemical Society, published on Web May 10, 2088.
B.T. Houseman, "Maleimide-Functionalized Self-Assembled Monolayers for the Preparation of Peptide and Carbohydrate Biochips", Langmuir 2003, 19, 1522-1531, 2003 American Chemical Society, published on Web Nov. 13, 2002.
M. Mrksich, "Mass Spectrometry of Self-Assembled Monolayers: A New Tool for Molecular Surface Science", ACS NANO, vol. 2, No. 1, 7-18, 2008, published online Jan. 22, 2008, www.acsnano.org, 2008 American Chemical Society.
A. Dhall, "Chemical Approaches to Understand the Language of Histone Modifications", ACS Chemical Biology, 2011, 6, 987-999, 2011 American Chemical Society.
E.P. Go, "Fluorous Based Affinity Mass Spectrometry", ASMS 2005.

* cited by examiner

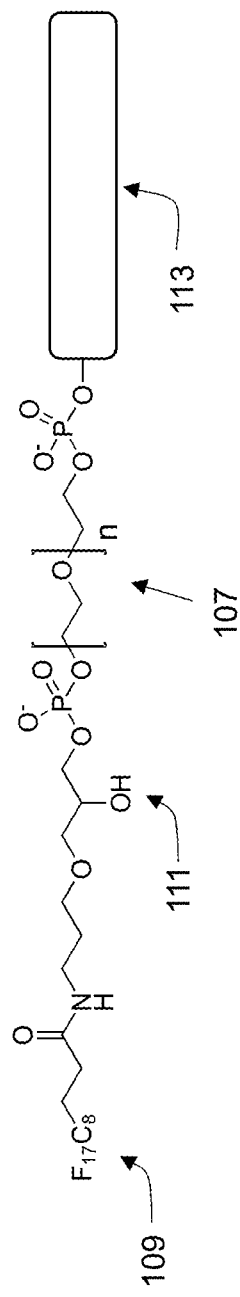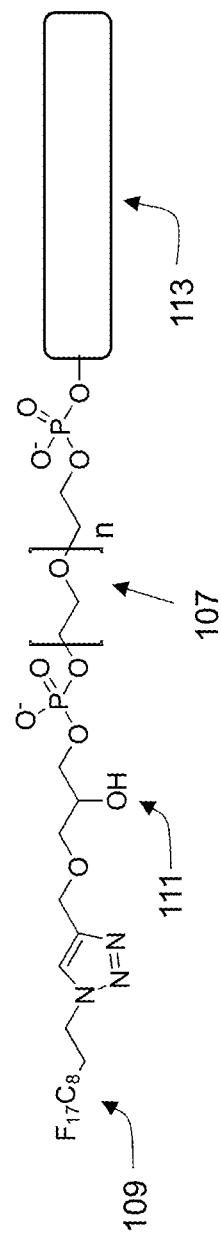

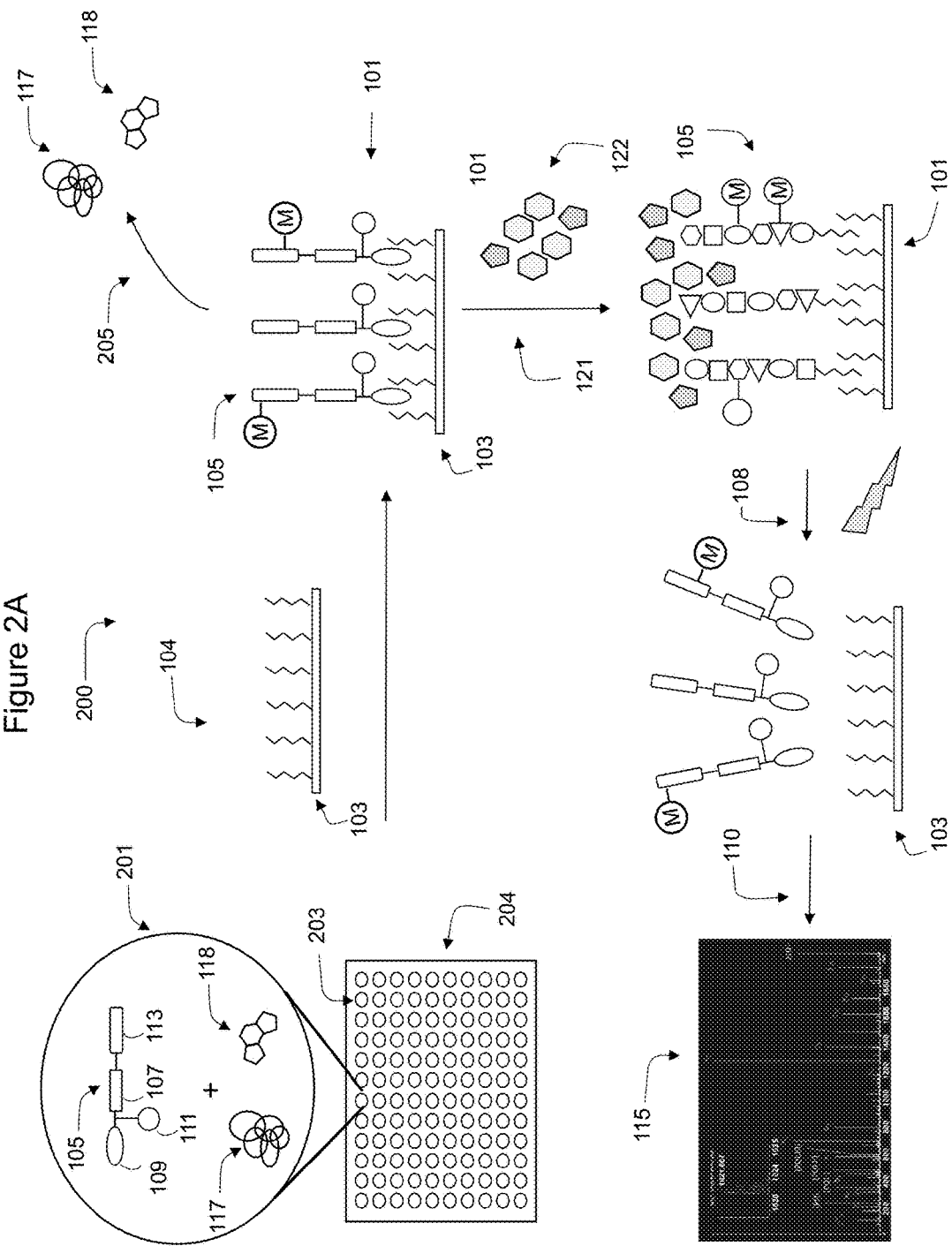

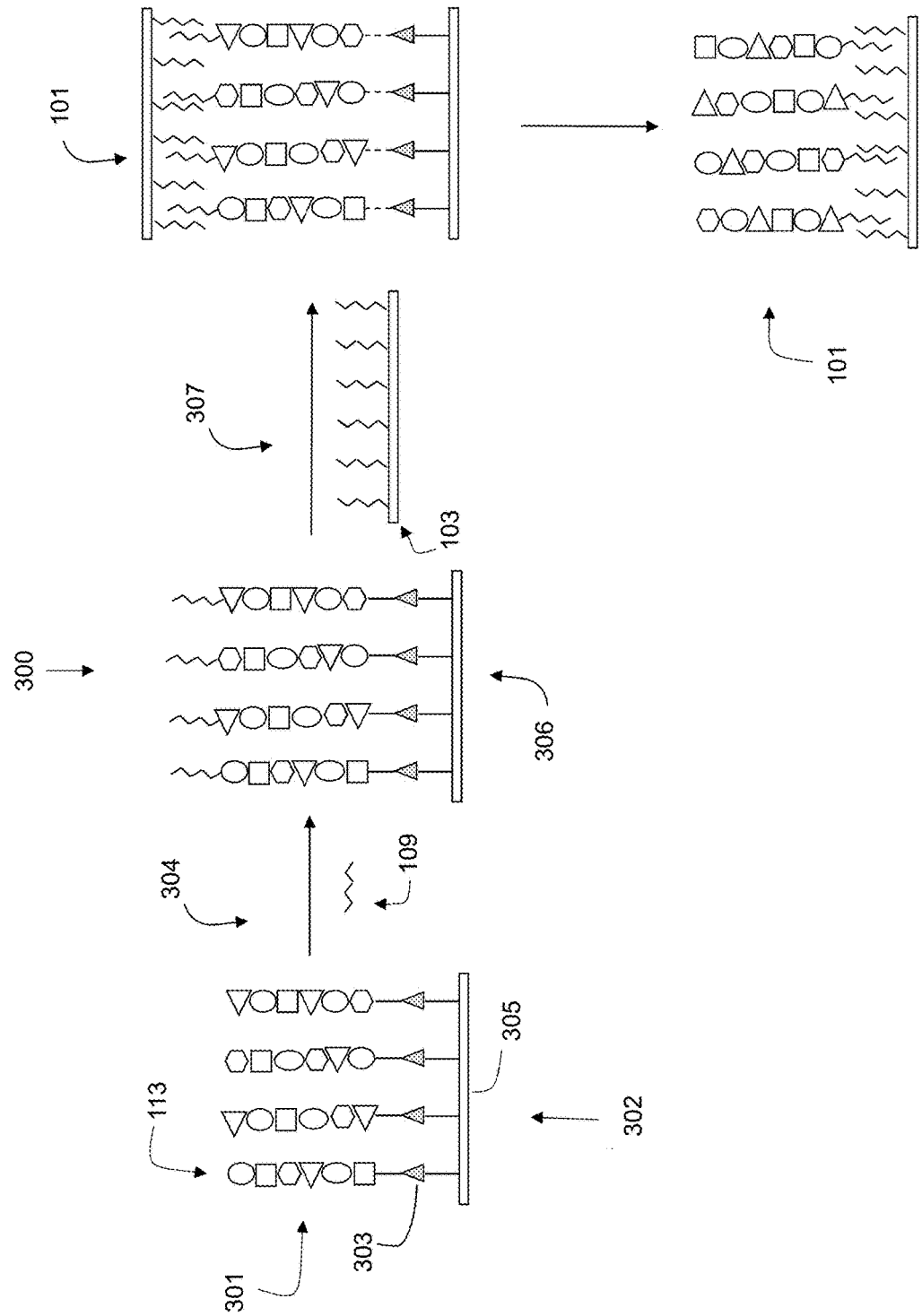

FLUOROUS OLIGONUCLEOTIDE MICROARRAY

CROSS-REFERENCE TO RELATED APPLICATIONS

This patent application claims the benefit of U.S. Provisional Patent Application Ser. No. 62/259,177 filed on Nov. 24, 2015 and entitled "Fluorous Microarray, Compositional Detection Process Using a Fluorous Microarray, and Process of Forming a Fluorous Microarray", the disclosure of which is hereby incorporated by reference herein in its entirety and made part of the present U.S. utility patent application for all purposes. This patent application is also a continuation-in-part of U.S. patent application Ser. No. 14/394,435 filed on Oct. 14, 2014, now U.S. Pat. No. 9,977,019, and entitled "Fluorous Peptide Microarray, Detection Process Using a Fluorous Peptide Microarray, and Process of Forming a Fluorous Peptide Microarray, the disclosure of which is incorporated by reference herein in its entirety and made part of the present U.S. utility patent application for all purposes.

BACKGROUND OF THE INVENTION

The present invention relates to compositions, structures formed by the compositions, processes of forming the compositions and the structures, and detection processes relying upon the compositions and structures. More specifically, the present invention relates to fluorous-modified nucleoside, nucleotide, and oligonucleotide arrays, fluorous-modified nucleoside, nucleotide, and oligonucleotide array preparation and detection processes, and fluorous-modified nucleoside, nucleotide, and oligonucleotide array compositions.

Nucleosides, nucleotides, and oligonucleotides are amongst the most important classes of chemical compounds in modern molecular biology, medicine, and drug discovery. Their importance is not only exemplified in DNA and RNA, which are both oligonucleotides, but also in nucleotides such as adenosine triphosphate (ATP), which is the primarily molecule used for cellular energy transfer, and in nucleoside analogs such acyclovir, an important antiviral drug. Additionally, these compounds, collectively referred to herein as "nucleotides," are of interest in many biological processes currently being explored for use in the diagnosis and treatment of various disease states. Accordingly, nucleotides are often used as substrates for the investigation of biomolecule interactions, small molecule inhibition of such interactions, and in the elucidation of biochemical pathways.

Assays and screens utilizing nucleotides as substrates or probes have become an integral part of the drug discovery and development process from target identification and validation through hit optimization and lead optimization. In addition, nucleotide-based diagnostics and therapeutics are increasing with nucleotide-based assays and screens playing an important role in drug development and clinical applications. The development of assays and screens using nucleotides as probes that provide high quality and high throughput is a continuing area of interest to the life sciences industry. However, there are many challenges to using nucleotides as molecular probes. One such challenge includes the unique chemical and physical properties of nucleotides, as compared to peptides, proteins, and carbohydrates, which are the other major classes of biologically relevant compounds.

There are a number of methods used currently for nucleotide-based assays. The standard methods are solution-phase-based methods using microtiter plates containing a number of wells generally ranging from 96 to 1536. The test solution and compounds along with a labeled nucleotide probe are added to each well. The label is generally a fluorogenic or chemiluminescent label which is necessary for detection. After the reaction is complete, the plate is scanned and those reactions which were positive can be distinguished from those that are negative through the fluorescent or chemiluminescent label. Microtiter-plate-based solution phase assays can often be conducted with very high throughput resulting in large data sets that are highly data dense. The primary shortcoming of these types of assays; however, is that the data is generally not of high quality.

Low data quality is generally due to the use of the fluorescent or chemiluminescent detection label. The label itself can oftentimes interfere with the native activity or selectivity of the nucleotide of interest. This results in a high rate of false positives and negatives. In addition, when adding test compounds that are potential drug candidates, fluorescence and chemiluminescence detection can be compromised either by autofluorescence or by interference from the test compound. It is common for 10% fluorescence interference rates to be reported when screening a library of compounds using assays of this type.

In addition, the information gathered by using fluorescent or chemiluminescent detection does not provide any structural information. Depending on the design of the assay, information such as the degree of change imparted on the nucleotide probe or the exact location of that change is lost. For example, in a ribose nucleic acid (RNA) screen, a variety of putative nucleotide substrates may be examined using a fluorogenic label. Cleavage of the RNA at the designed nucleotide location results in a positive signal. However, if hydrolytic activity were to take place concomitantly at other sites within the oligonucleotide backbone, a false positive signal would result providing an erroneous result. Alternatively, if two putative sites of cleavage were available on the nucleotide, a positive signal would indicate that some cleavage took place, but would not distinguish at which location. So, while the solution-phase-based assays can often be high throughput, they suffer from producing low-quality data which often requires extensive re-testing by other methods in order to confirm the results or to obtain additional information.

Another limitation of many solution phase assay systems is the inability to enrich the test sample for the analytes of interests. Analyte enrichment results in greater signal to noise, higher sensitivity, and lower issues with signal interference. This has led to the development of various labels designed to facilitate analyte enrichment in addition to detection, such as biotin-streptavidin, polyhistidine (His) tags, or solid phase tags. In the case of biotin or His tag labeled nucleotides, the labeled analytes can be enriched using the appropriate affinity support; streptavidin in the case of biotin and a nickel or cobalt based resin for His tags. However, many affinity based enrichment methods are limited by non-specific binding and lack of bioorthogonality, which gives rise to false signals requiring substantial follow-up experiments. For example, when using biotin-streptavidin based assays false signals can occur due to a number of factors including endogenous biotinylated molecules, biotin complexation with other proteins such as carboxylases, or streptavidin binding with other ligands besides biotin.

In contrast to solution-phase assays, the nucleotide probes in solid-phase assays are immobilized, usually through covalent bonding to a surface, for example, the bottom of a well within a microtiter plate or a three-dimensional solid such as a bead. The test solution containing the protein or enzyme, test compound, and/or other reaction components is added. Once the reaction is complete, the solution is removed and the well is washed to remove all other components leaving only the immobilized probe nucleotide. If the nucleotide is labeled, the fluorescence or chemiluminescent detection can be used as in the solution-phase assay.

The major advantage of the solid-phase method is that auto-fluorescent or fluorescence-interfering materials can be washed away reducing the number of false readouts. This does not, however, overcome limitations due to the presence of the label itself which may interfere with the action of the protein, enzyme, or other interacting entity nor does it provide additional structural information missing from the solution-phase assay.

Both solid-phase and solution phase assays may also use other detection methods. One known method is a radiometric method where a radioactive-isotope-labeled atom is incorporated into the nucleotide either before or after the desired reaction. Popular radioisotopes include $^{14}C$, $^{32}P$, $^{25}S$ and $^{152}I$. Radiometric methods are extremely sensitive and can oftentimes be quite specific. The major disadvantages are the special care and precautions necessary when using radioactive materials and the cost of the isotopes which can preclude use in early screening efforts. In addition radiometric detection provides no structural information such as the location of the radioisotope incorporation within the nucleotide nor does it provide a reliable measure of degree of radioisotope incorporation.

Another known detection method is a coupled assay which utilizes a second reaction in order to introduce a fluorescent or chemiluminescent label. In a coupled assay, label-free nucleotides can be used as the probe thereby avoiding any questions as to the effect of the label on activity. After the desired reaction is complete, a secondary reaction, generally using a labeled specific antibody, is conducted. The specific antibody only binds to the transformation in question, thereby providing the fluorescent signal. A solid-phase assay using a coupled antibody reaction therefore overcomes the problem of the labeled nucleotide probe and the interference issues often associated with solution-phase assays. Once again; however, it does not provide information-rich data.

In addition, the coupled assay can require introduction of appropriate surface chemistry in order to immobilize the probes. A large number of different surface chemistries have been introduced for probe immobilization including affinity-based such as biotin-streptavidin, and covalent bonding based as in maleimide, Diels-Alder, click chemistry, etc. Non-specific binding is also often a problem with these methods causing binding of other molecules besides the probe molecule to the surface compromising signal to noise ratio. For example, if the antibody used in the coupled assay non-specifically binds to the surface, then a false positive signal will be received. Also, the coupled assay is often dependent on the quality of the antibody which is a well-known problem in biological research as variability in antibody activity and selectivity, both inter- and intra-batch, introduces reproducibility and reliability issues in the data generated. In the absence of a highly selective antibody, the assay will once again result in a high number of false readouts. This lack of specific antibodies is in many areas considered to be one of the biggest shortcomings within the field.

Despite these drawbacks in information quality and robustness, solid-phase assays have found widespread use within the life sciences industry, primarily due to the high throughput that can be achieved, the epitome of which is the microarray where thousands of probes can be applied to a small surface and interrogated at once. Microarrays, including nucleotide microarrays, have been demonstrated extensively. Beyond the high throughput, the miniaturized format of microarrays allows minimal use of probe and reagents thereby reducing the overall cost per probe relative to microtiter-plate formats. The microarray format does not overcome the detection problems; however, of other assay formats.

An additional limitation of many of the above described methods are the expense of the fluorescent or chemiluminescent labels which add significant cost to utilizing these assays in the screening of large compound collections.

Other label-free detection methods include optical methods, such as surface plasmon resonance (SPR). SPR provides no structural information but is a sensitive method by which to observe changes in probes or to detect binding events. Even so, there are some transformations, such as phosphorylation, which SPR cannot reliably detect.

In order to address data quality and cost issues, researchers have turned primarily to mass spectrometry (MS) as a label-free detection method. Mass spectrometry is particularly well-suited for binding and activity assays since it can not only detect both starting probes and products, but also determine the degree of change on the probe and the location of the change. MS-based assays therefore provide informational richness that other detection methods do not afford leading to more robust data free from many of the issues faced using light-based detection methods. For example, a recent report of a high throughput screen found that using fluorescence detection 92% of positive signals were false and that converting the screen to MS detection reduced that false signal rate to the single digit range.

While providing high quality data, MS generally suffers from being only low to medium throughput. This is due primarily to the necessary sample preparation and purification in order to remove impurities and other unwanted materials from the sample which can adversely affect sensitivity and detection. A favored method to desalt a sample prior to MS is to use a solution-phase assay and liquid chromatography and MS (LC/MS). The chromatographic separation purifies the probe of interest so that it can then be analyzed by MS. This method; however, is very low throughput with each sample requiring a minute or more of time to analyze. Other methods, such as multiplexed (MUX) electrospray with parallel LC systems, have reduced the analysis time to as short as 30 seconds/sample, but still are orders of magnitude behind high-throughput assay methods. Another recent system includes a microfluidics-based desalting system coupled with MS detection. This system has been reported to process samples at a rate of one every 5-7 seconds which is significantly higher than other MS-based methods but still falls far short of fluorescence or radiometric-based systems.

Examples of assays which utilize a nucleotide with MS detection are kinase or phosphatase assays using adenosine triphosphate (ATP). Kinases transfer a phosphate from ATP to a protein therefore transforming ATP to ADP, adenosine diphosphate. The enzymatic activity can then be easily determined by the ATP:ADP ratio as determined by MS detection. Another example of MS detection of a nucleotide in a pharmaceutically relevant assay is the use of S-adenosyl methionine (SAM) in protein and peptide methylation. After methyl transfer, SAM is transformed into S-adenosyl homocysteine (SAH). Once again the level of enzymatic activity can be determined by measuring the SAM:SAH ratio. A significant advantage in these MS-based assays is that both the starting material and product levels can be measured which is generally not possible with other detection methods. Measuring only starting material consumption or product formation, but not both, can often lead to erroneous results including false positives and negatives should other processes than the desired one be occurring resulting in loss of starting material or accumulation of product.

In recent years there has been considerable effort to increase the throughput of MS analysis through the use of matrix-assisted laser desorption/ionization MS (MALDI-MS) or laser desorption/ionization MS (LDI-MS) which does not employ an external matrix. MALDI and LDI methods promise higher throughput than LC/MS methods and are particularly well-suited for the detection of various types of enzyme substrates, particularly peptides.

Unfortunately, the MALDI-MS detection of oligonucleotides is not as straightforward as that of peptides, primarily due to the presence of the phosphodiester linkage in the oligonucleotide backbone. The anionic phosphates render oligonucleotides highly prone to retaining salts and other contaminants thereby suppressing ionization, forming multiple mass species, and inducing gas phase fragmentation, all of which lead to poor sensitivity and reproducibility. This has led to a plethora of different desalting and matrix formulas and protocols designed to overcome the salt issue. Examples include the addition of co-matrices such as spermine, ammonium salts, or other polyamines, pre-treatment with anion exchange resins, or development of exotic matrix compounds. This is in direct contrast to MALDI-MS analysis of peptide or carbohydrate substrates which generally ionize readily through the addition of a simple single component matrix. The challenges in using MALDI-MS for high throughput screening with oligonucleotide probes is highlighted by the lack of such assay platforms relative to peptide based assays.

MALDI or LDI-MS based arrays have been developed in an attempt to combine the high-throughput of the microarray format with the high quality data of MS detection. A major difficulty in combining microarrays with MS detection is that methods for immobilization of nucleotide probes generally utilize covalent bonding formed by reaction of a reactive group on the nucleotide and a reactive group on the surface. The covalent bond formation allows the probes to be immobilized in a specific orientation and through a specific location on the nucleotide. Most covalently bound probes, however, cannot be ionized from the surface once the covalent bond is formed making it incompatible with direct MS detection. Non-covalent immobilization methods have also been used to form microarrays but generally lack specific display orientation which can affect substrate activity. There are, however, methods which can combine a microarray format with MS detection using non-covalent immobilization with specific display orientation.

A primary example of this would be self-assembled monolayer desorption/ionization MS (SAMDI-MS) where enzyme substrates are immobilized through the formation of alkanethiol monolayers on a gold surface. The substrates can then be reacted with the test solution of interest. A chemical matrix is then added to induce ionization and the probes are then analyzed by matrix-assisted laser desorption/ionization (MALDI-MS). SAMDI-MS then combines the high throughput of microarrays with the high quality data of MS detection.

The method, however, suffers from a number of deficiencies. First, results can be highly variable and dependent on the choice and application of the matrix. The optimal matrix can vary depending on the monolayer employed and the nature of the probes. Application of the matrix also needs to be precisely controlled in order to avoid inconsistencies and "patches" across the array resulting in areas of poor signal. In addition, the monolayers themselves may not be robust and are subject to degradation at elevated temperatures and upon exposure to UV light. These issues lead to questions regarding long-term storage and scalability, both critical items for commercialization.

Another limitation of SAMDI presents itself in the specific case of oligonucleotide probes. The SAMDI methods which were effective for peptide and carbohydrate immobilization and laser ionization proved to be completely ineffective when using oligonucleotide probes (Tsubery and Mrksich, *Langmuir*, 2008, 24, 5443). Formation of the self-assembled monolayer using thiol modified oligonucleotides occurred readily but ionization and detection by MS of the immobilized oligonucleotides using a variety of matrices proved completely unsuccessful. In order to utilize SAMDI for oligonucleotide probes it was necessary to first form a monolayer of biotin which was then reacted with streptavidin. The resultant streptavidin modified surface could then immobilize biotin modified oligonucleotides which could then be ionized from the surface after matrix addition. The use of biotin-streptavidin affinity, however, introduces its own issues including non-specific binding to both components. The unexpected difficulties in using oligonucleotide probes along with the cumbersome workaround has limited the utility of SAMDI in oligonucleotide applications. The authors noted that it was unclear why their previous protocols which worked effectively for other molecular classes (peptides, proteins, and carbohydrates) failed to do so for oligonucleotides. The work highlights the difficulty and unpredictability in applying prior MALDI-MS methods to oligonucleotides.

There have recently been efforts at avoiding some of the issues described. One method is to utilize fluorous partitioning where a highly fluorinated surface is used to immobilize perfluorocarbon modified substrates. Fluorous partitioning takes advantage of the fact that fluorous phases represent a third distinct phase from organic and aqueous phases and that fluorous tagged molecules partition preferentially and selectively into a fluorous phase. As such, the fluorous phase and fluorous tags are both hydrophobic and lipophobic. Since fluorous molecules are not biologically endogenous the use of fluorous partitioning is completely biorthogonal which is a highly desirable characteristic when conducting analyses from complex biological mixtures.

Fluorous partitioning has primarily been used as a separation technology in the synthesis and purification of various molecular classes including small molecules, peptides, carbohydrates, and oligonucleotides. In these applications, a temporary fluorous tag is attached to a molecule which can then undergo a series of synthetic reactions. The fluorous tagged molecule can then be separated from excess reagents and other non-tagged components through fluorous partitioning with either a liquid or solid fluorous phase. After removal from the fluorous phase, the fluorous tag can then be cleaved from the molecule providing the purified target molecule free from the fluorous tag. Alternatively, the desired target molecule can be non-tagged while reagents of undesired compounds can be fluorous tagged and a fluorous partition-based separation can be used to separate the target compound from the undesired compounds.

Fluorous partitioning has also been used for immobilization using a fluorous planar solid surface as the fluorous phase. Fluorous immobilization combines aspects of non-covalent and covalent immobilization. The probes are immobilized non-covalently through fluorous partitioning but in a specific display orientation through a specific end of the molecule; a characteristic usually reserved only for covalent bonding motifs. MS detection can then be conducted either through the use of a nano-structure initiated MS (NIMS) or directly off the surface, in some cases by laser ablation without the need of matrix. These non-matrix methods also have the advantage of being highly robust systems that require a minimum of special storage conditions.

To date fluorous partitioning has been used for the immobilization of fluorous tagged small molecules, peptides, and carbohydrates. Fluorous immobilization with direct MS detection has been reported for carbohydrates, but no reports of nucleoside, nucleotide or oligonucleotide immobilization or array formation using fluorous partitioning are extant either with or without direct MS detection, presumably due to the difficulties encountered in non-covalent immobilization and ionization of oligonucleotides.

Accordingly, it would be desirable to have materials, methods, and processes that do not suffer from one or more of the above drawbacks and would allow simultaneous assaying of a multitude of nucleotides with direct MS detection and facile analyte enrichment.

SUMMARY OF THE INVENTION

An exemplary embodiment of the present disclosure includes a process to form a fluorous nucleotide microarray with ionizable probes having a fluorous-modified conductive surface with a sheet resistivity of <50 ohm/square and fluorous nucleotides positioned on the fluorous-modified conductive surface in a compositional grid. Non-covalent fluorous partitioning immobilized probes provide specific display orientations of the fluorous nucleotides. The fluorous nucleotide probes are substrates for chemical compounds selected from the group consisting of a protein, an enzyme, a complementary nucleotide strand, and a ligand of interest. The immobilized probes are arranged and disposed for reaction with the protein, enzyme, complementary nucleotide strand, or ligand of interest followed by detection of any modification thereof upon matrix-assisted or matrix-free laser ionization of the probes into a mass spectrometry (MS) detector.

Another exemplary embodiment of the present disclosure includes a process to form a fluorous nucleotide microarray having a fluorous-modified conductive surface with a sheet resistivity of <50 ohm/square and fluorous nucleotides positioned on the fluorous-modified conductive surface a compositional grid that are immobilized after modification by a protein, enzyme, or ligand of interest either in the presence or without the presence of other reaction components which may modulate the action of the protein, enzyme, or ligand of interest. The mixture of the fluorous nucleotides, protein, enzyme or ligand of interest and other reaction components is then applied to the fluorous-modified conductive surface, the application immobilizing only the fluorous nucleotides to the fluorous-modified conductive surface through fluorous partitioning. The immobilized fluorous nucleotides are arranged and disposed for detection of modification through matrix-assisted or matrix-free laser ionization of the probes into a mass spectrometry (MS) detector.

Another exemplary embodiment of the present disclosure includes a compositional detection process. The process includes mass spectrometry analysis of a fluorous nucleotide microarray. The fluorous nucleotide microarray corresponds to a fluorous-modified composition having a linker, a nucleotide connected to the linker, and a fluorous domain connected to the linker. The compositional detection includes mass spectrometry analysis; the fluorous-modified composition includes at least one perfluoroalkyl group in the fluorous domain; the fluorous-modified composition may or may not include a solid-phase attachment group connected to the linker, or a combination thereof. The fluorous modification and linker may also be attached to the nucleotide either prior or subsequent to interaction with a protein, enzyme, or ligand or interest.

Another exemplary embodiment of the present disclosure includes processes of forming a fluorous nucleotide microarray. One process includes transfer blotting the fluorous-modified composition to form the fluorous nucleotide microarray. The fluorous-modified composition includes a linker, a nucleotide connected to the linker, and a fluorous domain connected to the linker. Another process includes the spotting and on-surface analyte enrichment of mixtures containing a fluorous-modified composition to form the fluorous nucleotide microarray.

Another exemplary embodiment of the present disclosure includes a fluorous-modified composition. The composition includes a linker, a nucleotide connected to the linker, and a fluorous domain connected to the linker. The linker and fluorous tag may be attached to the nucleotide through various positions and chemistries to the sugar unit (deoxyribose or ribose) or the pyrimidine or purine base, either directly or through the use of linker or side chain chemistry. The fluorous-modified composition includes at least one perfluoroalkyl group in the fluorous domain, and may or may not include a solid-phase attachment group connected to the linker, or a combination thereof.

Another exemplary embodiment of the present disclosure includes a fluorous nucleotide microarray process. The fluorous nucleotide microarray process includes using information corresponding to a compositional detection process in a method selected from the group consisting of identifying biological processes relevant to the detection, formation, or treatment of disease states, screening of compound collections for inhibitors or activators of biological processes of interest, diagnosing disease states within individuals for purposes of personalizing or monitoring treatment and disease progression, and combinations thereof.

Further aspects of embodiments of the invention are disclosed herein. The features as discussed above, as well as other features and advantages of the present application, will be appreciated and understood by those skilled in the art from the following drawings and detailed description.

BRIEF DESCRIPTION OF THE DRAWINGS

FIGS. 1B, 1C, 1D, 1E, 1F, 1G, and 1H show exemplary fluorous-modified compositions according to the disclosure.

FIG. 2A shows a schematic view of a process of forming a fluorous nucleotide microarray according to an embodiment of the disclosure, with structural transformation of the fluorous compositions by a protein, enzyme, or ligand occurring prior to immobilization. After immobilization matrix is added to enhance ionization and detection of the structural transformed fluorous compositions.

FIG. 3 shows a schematic view of a process of forming a fluorous nucleotide microarray according to an embodiment of the disclosure.

Wherever possible, the same reference numbers will be used throughout the drawings to represent the same parts.

DETAILED DESCRIPTION OF EXEMPLARY EMBODIMENTS

Provided is a fluorous nucleotide microarray, a compositional detection process, a process of forming a fluorous nucleotide microarray, a fluorous-modified composition, and a fluorous nucleotide microarray process. Embodiments of the present disclosure, for example, in comparison to concepts failing to include one or more of the features disclosed herein, result in greater protocol flexibility (for example on-surface or off-surface enzymatic reaction, tagging before or after enzymatic reaction), permit acquisition of denser data during detection (for example, by having high throughput), permit acquisition of more information during detection (for example, higher quality information, structural information, and/or information not available through other microarray techniques), result in lower false readouts for detection (for example, by reducing or eliminating antibodies and other coupled reactions), simplify workflows in the formation of arrays (for example, by eliminating blocking and washing steps or the use of an added matrix as is done in existing techniques corresponding to SAMDI), eliminate the need for bioaffinity based immobilization such as biotin-streptavidin based immobilization, or combinations thereof.

Figure 1:
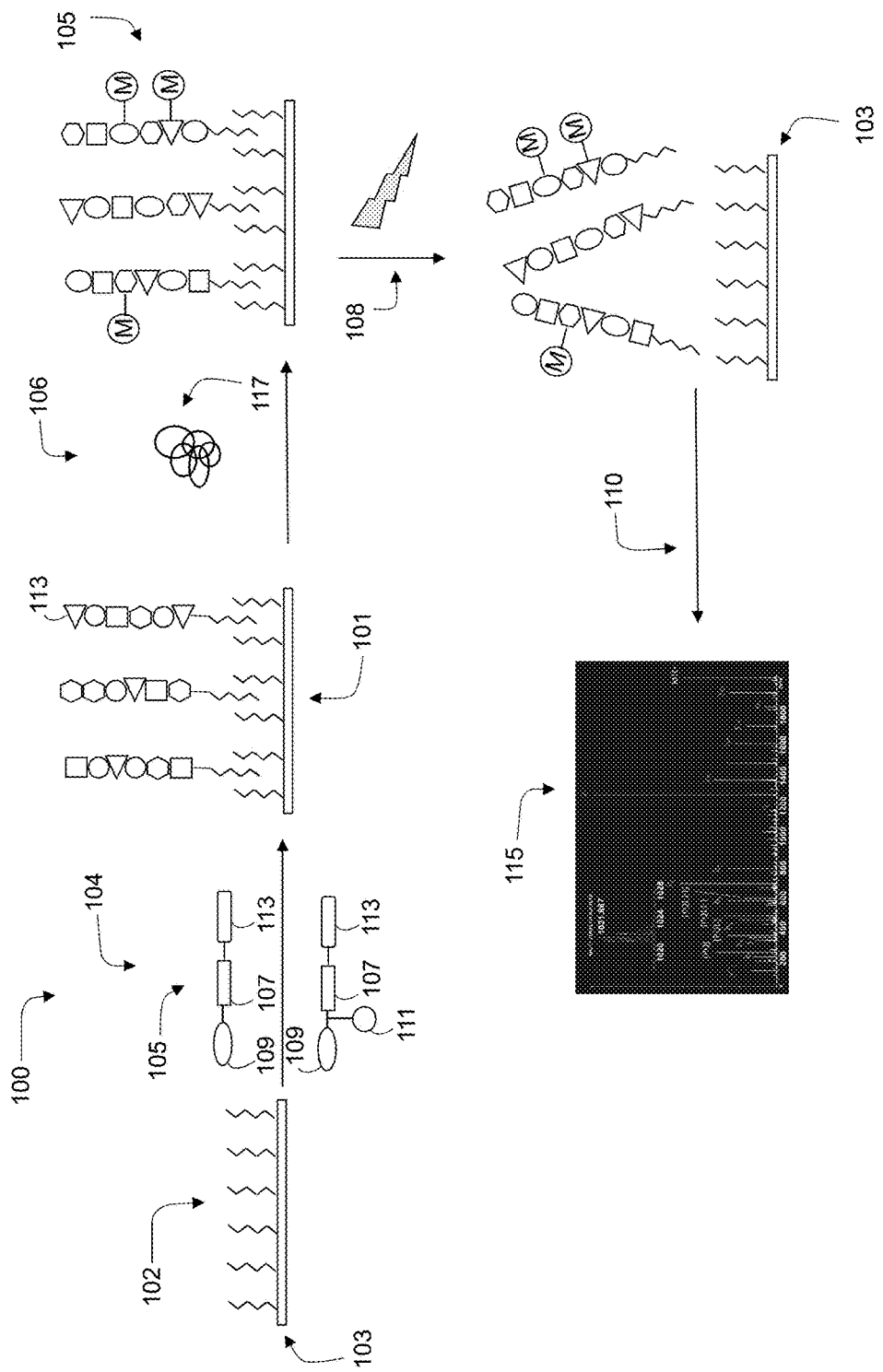
FIG. 1 shows a schematic view of an exemplary process of forming an exemplary fluorous nucleotide microarray according to the disclosure with structural transformation of the fluorous compositions by a protein, enzyme, or ligand occurring subsequent to immobilization with ionization, and detection occurring after the structural transformation.

FIG. 1 shows an embodiment of a process 100 of forming a fluorous nucleotide microarray 101. As used herein, the term "nucleotide" refers to a nucleoside, a nucleotide, an oligonucleotide, or a combination thereof. In one embodiment, the process 100 includes providing a fluorous-modified conductive surface 103 (step 102) and applying a fluorous-modified composition 105 (step 104) to the fluorous-modified surface 103. The fluorous-modified surface 103 is any suitable fluorous-modified or perfluorinated conductive surface, such as, a surface formed by chemical vapor deposition of a fluorous agent. The fluorous-modified composition 105 includes any suitable fluorous-modified composition, such as, but not limited to, a fluorous-tagged nucleotide. The fluorous modified compositions 105 are arranged in a compositional grid on fluorous modified surface 103 to provide a fluorous nucleotide microarray 101 with each fluorous modified composition individually occupying a defined location within the grid. In a further embodiment, the process includes exposing the fluorous nucleotide microarray 101 to a protein complex 117 (step 106) which induces a chemical change to one or more of the fluorous modified compositions. The fluorous-modified compositions 105 are then individually laser ionized from the fluorous-modified surface 103 (step 108) and analyzed with a mass spectrometer detector (step 110), which provides mass spectrum 115 as the output.

Figure 1A:
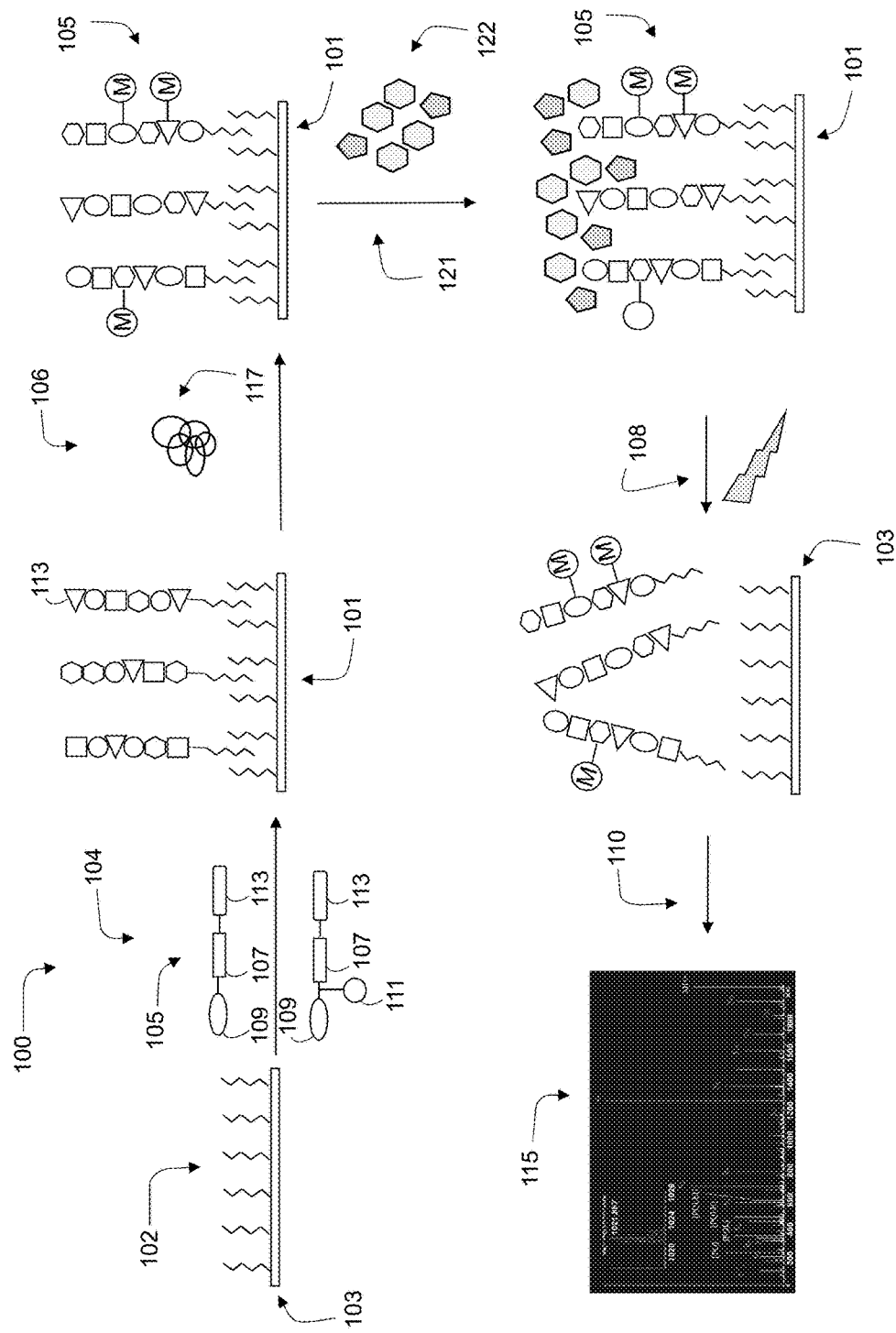
FIG. 1A shows a schematic view of an exemplary process of forming an exemplary fluorous nucleotide microarray according to the disclosure with structural transformation of the fluorous compositions by a protein, enzyme, or ligand occurring subsequent to immobilization. After structural transformation matrix is added to enhance ionization and detection of the structural transformed fluorous compositions.
Figure 1E:
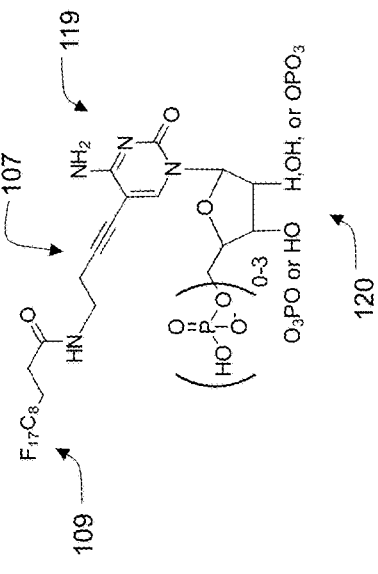
Figure 1D:
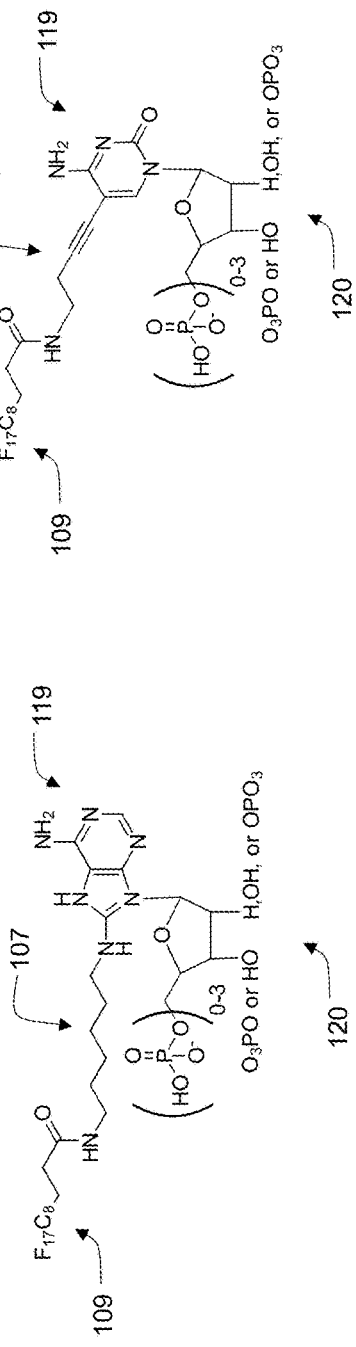
Figure 1G:
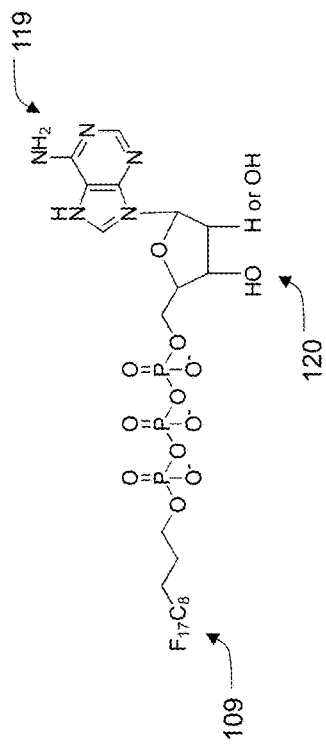
Figure 1F:
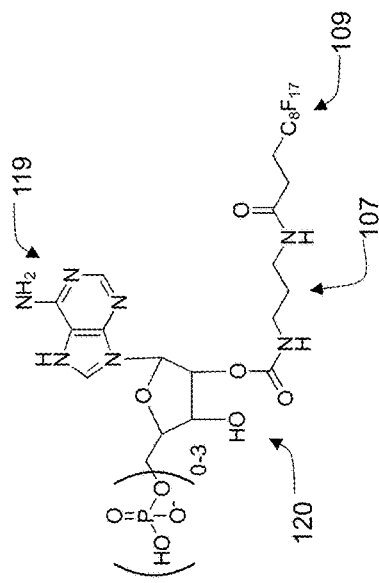
Figure 1H:
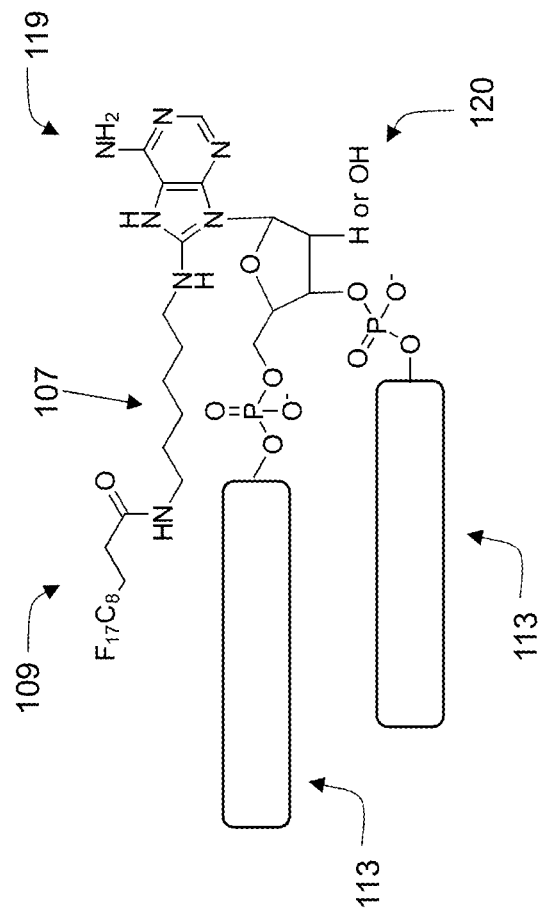

FIG. 1A shows an embodiment of the process depicted in FIG. 1 with the additional step of matrix addition (step 121). The matrix 122 consists of one or more compounds in a solvent system which contains a fluorophilic solvent that is applied to the fluorous microarray 101. The fluorophilic solvent is a partially fluorinated alkane, alcohol, ester, or ether. After evaporation of the solvent the fluorous-modified compositions 105 are then individually laser ionized from the fluorous-modified surface 103 (step 108) and analyzed with a mass spectrometer detector (step 110) by matrix-assisted laser desorption-ionization, which provides mass spectrum 115 as the output.

The applying of the fluorous-modified composition 105 to the fluorous-modified conductive surface 103 secures at least a portion of the fluorous-modified composition 105 to the fluorous-modified conductive surface 103 through fluorous partitioning, forming the fluorous nucleotide microarray 101. One suitable method of applying the fluorous-modified composition 105 or a plurality of fluorous-modified compositions 105 to the fluorous-modified surface 103 includes, for example, spotting and/or transfer blotting. Generally, spotting includes independently preparing solutions having the fluorous-modified composition 105 and individually spotting the solutions to the fluorous-modified surface 103 to form the fluorous nucleotide microarray 101. Transfer blotting, as is further described below with reference to FIG. 4, generally includes using in situ methods, such as simultaneous oligonucleotide synthesis on membranes, glass, or other modified solid phases, or nucleotide laser printing. In one embodiment, the transfer blotting includes attaching portions of the fluorous-modified composition 105 to nucleotides to form an embodiment of the fluorous nucleotide microarray 101 that is not immobilized by fluorous partitioning.

The fluorous-modified surface 103 is arranged and disposed to immobilize one or more fluorous-modified nucleotides through fluorous partitioning. For example, in one embodiment, the fluorous-modified composition 105 includes at least one nucleotide having a terminal and/or internal fluorous tag that immobilizes the nucleotide onto the fluorous-modified surface 103. In another embodiment, the fluorous-modified composition 105 includes a linker 107, a nucleotide 113 connected to the linker 107, and a fluorous domain 109 connected to the linker 107. As used herein, the term "connected" is direct or indirect and refers to covalent bonding, ion pairing, other close chemical associations, or a combination thereof. Embodiments of the fluorous-modified composition 105 may further include a solid-phase attachment group 111, may be devoid of the solid-phase attachment group 111, and/or may have any suitable combination of the linker 107 and the fluorous domain 109, for example, as is shown with the specific embodiments of the fluorous-modified composition 105 in FIGS. 1B-1H. Additionally or alternatively, the fluorous domain 109 and the linker 107 include other groups or moieties that provide reactive groups to covalently bond or ionically pair the linker 107, the fluorous domain 109, the nucleotide 113, or a combination thereof. Suitable reactive groups include, but are not limited to, carboxylic acids, amines, thiols, phosphines, maleimides, halides, alkynes, and azides.

The linker 107 and the fluorous domain 109 may be attached to the nucleoside, nucleotide, or oligonucleotide at various points of attachment including either the nitrogenous base 119 or the sugar moiety 120. Additionally, the linker 107 and the fluorous domain 109 may be attached at various positions on either base 119 or sugar 120, at a terminal position of the nucleotide 113, and/or at an internal position of the nucleotide 113. The nitrogenous base 119 may be any of the various purine or pyrimidine bases such as thymine, adenine, guanine, uracil, or cytosine all of which may be modified at various locations on the base and also include analogs of these bases. The sugar 120 can include various carbohydrate moieties including, but not limited to, ribose, deoxyribose, phosphorylated or other modified versions of sugars such as fluorinated versions, allylated or acylated versions, and other functionalized sugars.

The linker 107 connects components of the fluorous-modified composition 105. In one embodiment, the linker 107 includes or is a diamine linker. A non-limiting example of the linker 107 has the following molecular structure:

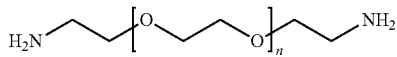

In one embodiment, the linker 107 has an n-value of between 0 and 5. In further embodiments, the linker 107 has an n-value of between 0 and 1, between 0 and 2, between 0 and 3, between 0 and 4, between 1 and 2, between 1 and 3, between 1 and 4, between 1 and 5, between 2 and 3, between 2 and 4, between 2 and 5, between 3 and 4, between 3 and 5, between 4 and 5, 1, 2, 3, 4, or 5.

Another non-limiting example of the linker 107 includes or has the following molecular structure:

In one embodiment, the linker 107 has an n-value of between 0 and 20. In further embodiments, the linker 107 has an n-value of between 0 and 20, between 0 and 5, between 0 and 10, between 0 and 15, between 5 and 10, between 5 and 15, between 5 and 20, between 10 and 15, between 10 and 20, 5, 10, 15, 20, or any suitable combination, sub-combination, range, or sub-range thereof.

A non-limiting example of the fluorous domain 109 includes or has the following molecular structure:

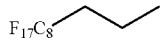

Another non-limiting example of the fluorous domain 109 includes or has the following molecular structure:

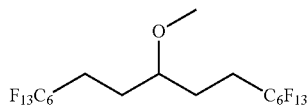

In one embodiment, the fluorous-modified composition 105 includes at least three terminal perfluoroalkyl groups in the fluorous domain 109 (for example, having the general formula of $C_nF_{2n+1}$). A non-limiting example of the fluorous domain 109, according to this embodiment, includes or has the following molecular structure:

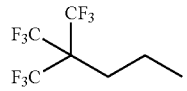

Another non-limiting example of the fluorous domain 109, according to this embodiment, includes or has the following molecular structure:

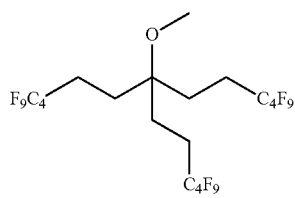

Non-limiting examples of the solid-phase attachment group 111 include or portions of the solid-phase attachment group 111 carboxylic acid and dicarboxylic acid.

Figure 2:
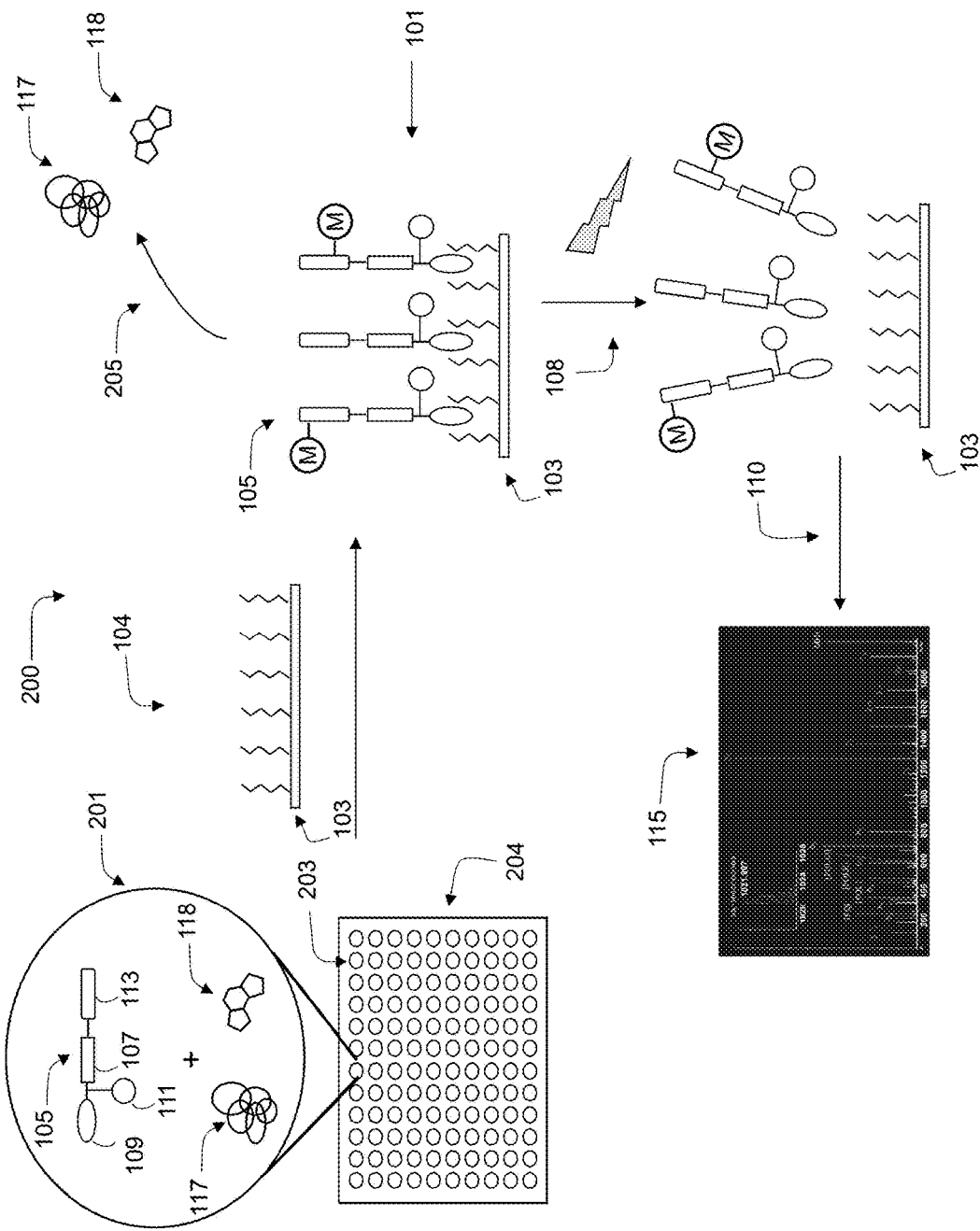
FIG. 2 shows a schematic view of a process of forming a fluorous nucleotide microarray according to an embodiment of the disclosure, with structural transformation of the fluorous compositions by a protein, enzyme, or ligand occurring prior to immobilization and detection occurring after immobilization to the fluorous surface.

FIG. 2 shows an embodiment of a process 200 of conducting a reaction 201 including but not limited to the fluorous-modified composition 105, protein, protein complex, or enzyme 117, and may include test compound 118. Reaction 201 is conducted within a well or confined area 203 as part of multi-well plate 204. The contents of well 203 or an aliquot of the contents of well 203 and other wells on plate 204 are spotted in discrete defined areas on fluorous-modified surface 103 (step 104) to form fluorous nucleotide microarray 101 by fluorous partitioning. Protein, protein complex, or enzyme 117 and test compound 118 are selectively washed away from the fluorous nucleotide microarray 101 (step 205) providing enrichment of the fluorous-modified composition 105. The fluorous-modified compositions 105 are then individually laser ionized from the fluorous-modified surface 103 (step 108) and analyzed with a mass spectrometer detector (step 110), providing mass spectrum 115 as the output.

FIG. 2A shows an embodiment of the process depicted in FIG. 2 with the additional step of matrix addition (step 121). The matrix (122) consists of one or more compounds in a solvent system which contains a fluorophilic solvent that is applied to the fluorous microarray 101. The fluorophilic solvent is a partially fluorinated alkane, alcohol, ester, or ether. After evaporation of the solvent the fluorous-modified compositions 105 are then individually laser ionized from the fluorous-modified surface 103 (step 108) and analyzed with a mass spectrometer detector (step 110) by matrix-assisted laser desorption-ionization, which provides mass spectrum 115 as the output.

FIG. 3 shows an embodiment of a process 300 of forming the fluorous nucleotide microarray 101. The process 300 includes providing an array 301 (step 302) that includes at least one cleavable linker 303 connecting a solid-phase surface 305 to one or more of the nucleotides 113, and applying the fluorous domain 109 to the nucleotide(s) 113 (step 304) to form an array of covalently bound fluorous-modified nucleotides 306. A fluorous-modified surface 103 is applied under conditions that cleave the cleavable linker 303 (step 307), thereby forming the fluorous nucleotide microarray 101. Non-limiting cleavage conditions include acidic, basic, photocleavable, or enzymatic conditions. The fluorous-modified surface 103 may be the same as or different from the fluorous-modified surface 103 shown and described in reference to FIG. 1.

Figure 4:
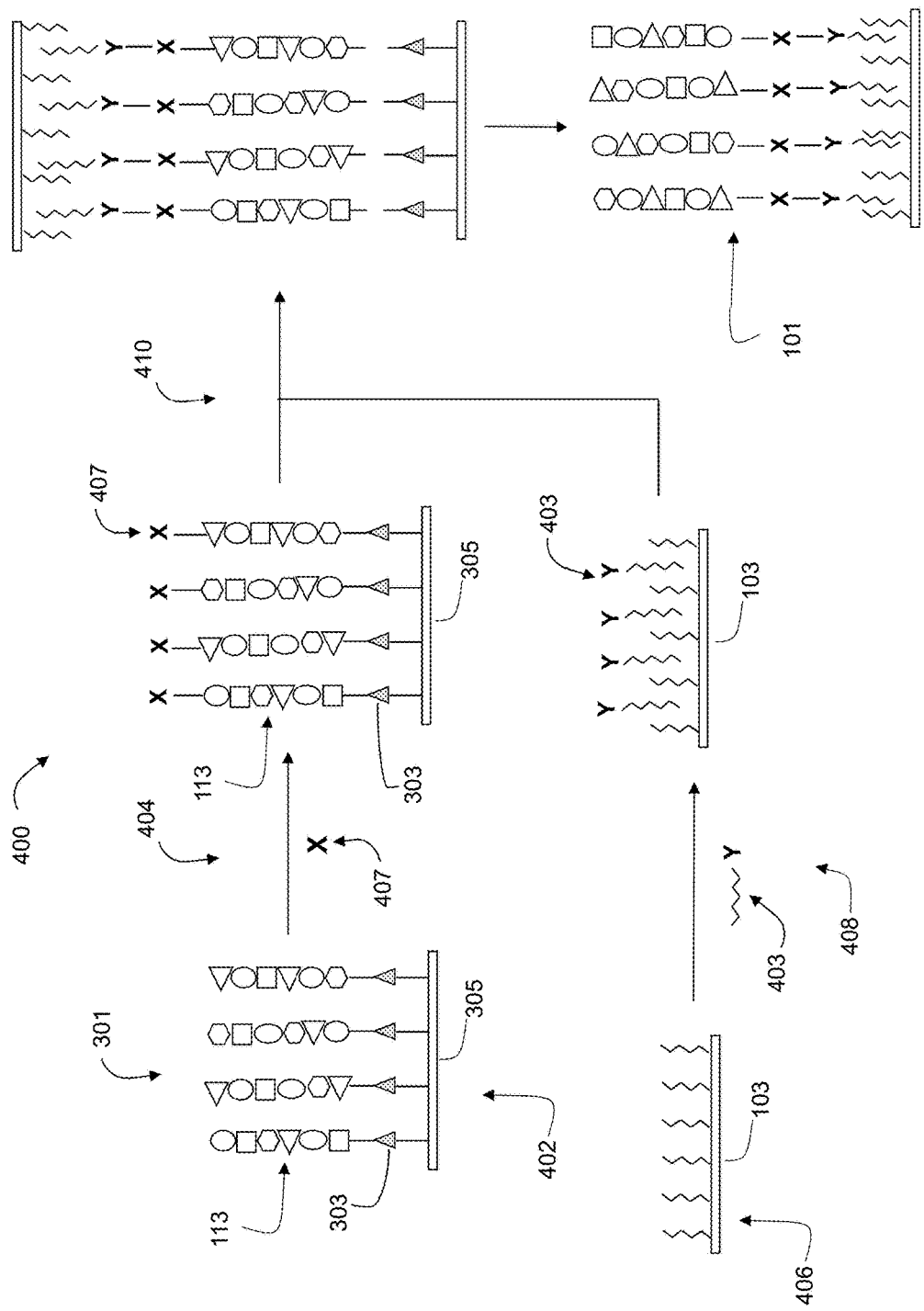
FIG. 4 shows a schematic view of a process of forming a fluorous nucleotide microarray according to an embodiment of the disclosure.

FIG. 4 shows an embodiment of a pre-coat process 400 of forming the fluorous nucleotide microarray 101. The process 400 includes providing an array 301 (step 402) produced by known nucleotide array methods and including at least one cleavable linker 303 connecting a solid-phase surface 305 to one or more of the nucleotides 113, and applying a reactive group 407 to the nucleotide(s) 113 (step 404). Separately, the covalently-modified fluorous conductive surface 103 is provided (step 406) and a fluorous-modified reactive group 403 is applied to the fluorous-modified surface 103 (step 408), thereby forming an embodiment of the fluorous-modified conductive surface 103 with the reactive group 403 immobilized within by fluorous partitioning. The fluorous-modified surface 103 is applied to the array 301 under simultaneous reactive-cleaving conditions (step 410), thereby forming the fluorous nucleotide microarray 101 by concomitant cleavage from solid-phase surface 305 and reaction between 407 and 403 to form array 101. The fluorous-modified surface 103 may be the same as or different from the fluorous-modified surface 103 shown and described in reference to FIG. 1.

Referring again to FIG. 1, in one embodiment, the process 100 of forming the fluorous nucleotide microarray 101 further includes protein, protein complex, enzyme, or ligand modification of the nucleotide 113 (step 106). The content of the fluorous nucleotide microarray 101 is adjustable depending upon the nucleotide, protein or enzyme and assay of interest. The enzyme modification may include using any suitable enzyme capable of mediating a chemical reaction or modification of a nucleotide. Suitable enzymes include, but are not limited to, kinases, methyltransferases, transcriptases, enzymes associated with cancer, enzymes associated with Alzheimer's, enzymes associated with diabetes, ligases, DNAses, RNAses, phosphatases, proteases, esterases, glycosyl transferases, hydrolases, polymerases, nucleases, helicases, other enzymes capable of facilitating modifications, or combinations thereof. Proteins may include, but are not limited to, transcription factors, binding proteins, and readers. Ligands may include, but are not limited to, various forms of RNA and DNA, such as mRNA, siRNA, shRNA, and ssDNA, and PNAs.

In one embodiment, the fluorous nucleotide microarray 101 includes a series or library of fluorous-modified nucleotide sequences which are immobilized in a spatially segregated defined pattern onto a fluorous-modified surface.

In one embodiment, the fluorous nucleotide microarray 101 includes features corresponding to being formed through deposition of fluorous tagged nucleotides that are prepared using blotting fluorous-modified or other techniques that had been prepared in situ on a non-fluorous surface.

In one embodiment, the fluorous nucleotide microarray 101 is formed by deposition of a reaction mixture containing a fluorous tagged nucleotide that is immobilized on the fluorous conductive surface while other reaction components are not immobilized. The fluorous conductive surface with the immobilized fluorous nucleotides is then washed to remove the non-immobilized components resulting in analyte enrichment. Non-fluorous tagged reaction components washed away may include salts, detergents, and buffers, enzymes and proteins, test compounds of interest that may be potential inhibitors or activators of the enzyme and protein.

In one embodiment, the fluorous nucleotide microarray 101 includes a chemically inert surface suitable for mass production. Suitable surfaces include, but are not limited to, fluorous-modified or perfluorinated conductive surfaces such as metal oxide surfaces, silicon black, graphene or graphene oxide, self-assembled monolayers, and nanostructured surfaces.

The content of the fluorous nucleotide microarray 101 is adjustable depending upon the nucleotide, protein or enzyme and assay of interest. Suitable classes include, but are not limited to, kinases, phosphatases, proteases, ligases, transcription factors, esterases, glycosyl transferases, hydrolases, methyltransferases, polymerases, nucleases, helicases, DNAses, RNAses, or combinations thereof. The fluorous nucleotide content of the microarray 101 can include varying sequences of DNA or RNA or identical sequences with differing marks or modifications such as methylated nucleotides.

Any suitable enzyme, protein, or nucleotide capable of mediating a chemical reaction or modification of a nucleotide may be investigated using the fluorous nucleotide microarray 101. Examples of a chemical reaction or modification include, but are not limited to, ligation, phosphorylation, methyl transfer, acylation, glycosylation, truncation, hydrolysis, or hybridization. The types of assays that can be conducted include, but are not limited to, genotyping, single nucleotide polymorph detection, tiling array, gene expression profiling, substrate profiling, selectivity and activity determination, inhibition assays, nucleotide binding, and counterscreens.

Referring again to FIG. 1, in one embodiment, compositional detection is performed (step 108). The compositional detection (step 108) may be performed as part of the process 100 shown in FIG. 1 or independently. The compositional detection (step 108) includes mass spectrometry analysis using the fluorous nucleotide microarray 101. Additionally or alternatively, the compositional detection (step 108) includes other analytical methods.

In one embodiment, the compositional detection (step 108) includes analyzing marks, for example, by using mass spectrometry, without the addition of a matrix. In another embodiment, the composition detection (step 108) identifies information about the modifications on the nucleotides. In a further embodiment, the information includes direct readouts, data, plots, chromatograms 115, or combinations thereof corresponding to the nucleotides 113 of the fluorous nucleotide microarray 101. After analyzing and/or identifying, the information is gathered, stored, and/or used (step 110). The use (step 110) of the information includes transmitting the information, receiving the information, relying upon the information, instructing others based upon the information, or a combination thereof. The use of the information for the elucidation of biological processes important to disease state, formation, treatment, or diagnosis such as cancer includes, for example, identifying enzyme activities which are enhanced or suppressed in cancerous cells compared to non-cancerous cells. These enzymes are then important as potential biomarkers of cancer, targets for tumor treatment, or indicators of response to treatment. Another example is the screening of compound collections to identify molecular entities that inhibit or activate biological processes of interest for the treatment of disease states such as the identification of oncogene suppressors or activators of tumor suppressing genes. A further example is the use of the information as a diagnostic tool in personalized medicine where the information can be used to identify therapies individualized for optimal response or to monitor disease response and progression as a result of medical intervention.

In one embodiment, prior to the compositional detection (step 108), the fluorous nucleotide microarray 101 is incubated with a test solution (for example, including or not including the enzymes and/or proteins). In another embodiment, the incubation of the fluorous nucleotide microarray 101 with the test solution generates one or more of the modifications described herein. For example, in a further embodiment, the fluorous nucleotide microarray 101 is incubated in the presence of purified enzymes or cell lysates, the purified enzymes or cell lysates structurally changing the fluorous nucleotide microarray 101 through addition, elimination, dephosphorylation, phosphorylation, and/or methylation to form the modifications. The modifications may be interrogated by laser desorption/ionization and analyzed by the mass spectrometry, for example, to confirm that a change in the nucleotide 113 has taken place due to action of the enzyme and/or the protein or that an enzyme and/or protein-ligand binding complex has been formed. The compositional detection (step 108) may further provide information regarding nucleotide residue on which an enzymatic reaction took place.

The types of assays that can be conducted include, but are not limited to, genotyping, single nucleotide polymorph detection, tiling array, gene expression profiling, substrate profiling, compound screening, selectivity and activity determination, inhibition assays, protein binding and counterscreens.

While only certain features and embodiments of the invention have been shown and described, many modifications and changes may occur to those skilled in the art (for example, variations in sizes, dimensions, structures, shapes and proportions of the various elements, values of parameters (for example, temperatures, pressures, etc.), mounting arrangements, use of materials, colors, orientations, etc.) without materially departing from the novel teachings and advantages of the subject matter recited in the claims. The order or sequence of any process or method steps may be varied or re-sequenced according to alternative embodiments. It is, therefore, to be understood that the appended claims are intended to cover all such modifications and changes as fall within the true spirit of the invention. Furthermore, in an effort to provide a concise description of the exemplary embodiments, all features of an actual implementation may not have been described (i.e., those unrelated to the presently contemplated best mode of carrying out the invention, or those unrelated to enabling the claimed invention). It should be appreciated that in the development of any such actual implementation, as in any engineering or design project, numerous implementation-specific decisions may be made. Such a development effort might be complex and time consuming, but would nevertheless be a routine undertaking of design, fabrication, and manufacture for those of ordinary skill having the benefit of this disclosure, without undue experimentation.

What is claimed is:

1. A microarray for detecting targets and biomolecule interactions, comprising:
   (a) a covalently-modified electrically conductive fluorous surface comprising a compositional grid,
      (i) wherein the surface is electrically conductive with a sheet resistivity of less than 50 ohms/square, and
      (ii) wherein the electrically conductive surface is perfluorocarbon modified;
   (b) a plurality of fluorous-modified oligonucleotide compositions, wherein each fluorous-modified oligonucleotide composition in the plurality of fluorous-modified oligonucleotide compositions includes:
      (i) a terminal fluorous domain or tag comprising at least one perfluoroalkyl group in the fluorous domain or tag, wherein the terminal fluorous domain or tag immobilizes each fluorous-modified oligonucleotide composition on the perfluorocarbon covalently-modified electrically conductive surface by non-covalently interacting with the perfluorocarbon modified surface through fluorous partitioning, wherein a fluorous-modified oligonucleotide composition occupies a defined location within the grid;
      (ii) a linker connected to the terminal fluorous domain or tag, wherein the linker is a diamine linker, a phosphonic acid-hydroxyl linker, or an alkynyl amine linker; and
      (iii) an oligonucleotide connected to the linker, wherein the oligonucleotide is configured to bind targets and interact with biomolecules of interest;
   (c) wherein the presence of a target bound to the oligonucleotide in the fluorous-modified oligonucleotide composition or biomolecule interaction with the oligonucleotide in the fluorous-modified oligonucleotide composition is detectable by mass spectrometry through individual laser ionization of the oligonucleotide fluorous-modified composition immobilized on the perfluorocarbon covalently-modified electrically conductive surface.

2. The microarray of claim 1, wherein the covalently-modified electrically conductive fluorous surface is selected from the group consisting of a fluorous-modified indium tin oxide, fluorous-modified metal oxide, fluorous-modified silicon, a fluorinated nano-structured surface, fluorous-modified graphene surface, fluorous-modified graphene oxide surface, and combinations thereof.

3. The microarray of claim 1, wherein the fluorous-modified oligonucleotide compositions are substrates for kinases, transcriptases, reverse transcriptases, proteases, glycosyl transferases, phosphatases, methyltransferases, ligases, RNAses, DNAses, or other oligonucleotide modifying enzyme.

4. The microarray of claim 1, wherein a subset of the target bound to the oligonucleotide is a reversible or irreversible binding partner for transcription factors, proteins or protein complexes, peptides, or oligonucleotides of biological interest.

5. The microarray of claim 1, wherein the fluorous-modified oligonucleotide compositions are a component of a mixture of compounds used in an enzymatic, protein binding, or ligand binding reaction prior to positioning on the fluorous-modified conductive surface.

* * * * *